US006521661B1

(12) United States Patent
Chen et al.

(10) Patent No.: US 6,521,661 B1
(45) Date of Patent: Feb. 18, 2003

(54) CYCLIC PEROXIDES AS NOVEL ANTIFUNGAL AGENTS

(75) Inventors: Ying Chen, Vero Beach, FL (US); Katherine Chilson, Louisville, CO (US); Keith Brian Killday, Fort Pierce, FL (US); Dedra Harmody, Vero Beach, FL (US); Peter J. McCarthy, Vero Beach, FL (US); Shirley A. Pomponi, Fort Pierce, FL (US); Rebecca Schimoler, Boulder, CO (US); Claude Selitrennikoff, Evergreen, CO (US); Amy E. Wright, Fort Pierce, FL (US)

(73) Assignees: Harbor Branch Oceanographic Institution, Inc., Fort Pierce, FL (US); Mycologics, Inc., Denver, CO (US)

( * ) Notice: Subject to any disclaimer, the term of this patent is extended or adjusted under 35 U.S.C. 154(b) by 0 days.

(21) Appl. No.: 09/909,681

(22) Filed: Jul. 20, 2001

Related U.S. Application Data

(60) Provisional application No. 60/219,519, filed on Jul. 20, 2000.

(51) Int. Cl.$^7$ .................... A61K 31/357; C07D 317/04; C07D 319/02
(52) U.S. Cl. ........................ 514/452; 514/467; 549/357; 549/430
(58) Field of Search ................................ 514/452, 467; 549/357, 430

(56) References Cited

U.S. PATENT DOCUMENTS

| | | | |
|---|---|---|---|
| 4,731,377 A | 3/1988 | Higa et al. ................... | 514/452 |
| 4,801,606 A | 1/1989 | Higa et al. ................... | 514/452 |
| 4,808,590 A | 2/1989 | Higa et al. ................... | 514/272 |
| 4,879,307 A | 11/1989 | Patil ............................ | 514/467 |
| 5,328,929 A | 7/1994 | Pettit et al. .................. | 514/462 |
| 5,393,897 A | 2/1995 | Pettit et al. .................. | 549/267 |
| 5,436,400 A | 7/1995 | Pettit et al. .................. | 549/267 |
| 5,883,120 A | 3/1999 | Pettit .......................... | 514/450 |

OTHER PUBLICATIONS

Bloodworth, A. J.; Bothwell, B. D.; Collins, A. N.; Maidwell, N. L. (1996) "A Short Synthesis of Naturally Occurring and Other Analogues of Plakinic Acids that Contain the 1,2–Dioxolane Group" *Tetrahedron Let.* 37:1885–1888.

Braekman, J. C.; Daloze, D.; Groote, S. D.; Fernandes, J. B.; Van Soest, R. W. M. (1998) "New Polyketides from the Sponge Plakortis sp." *J. Nat. Prod.* 61:1038–1042.

Compagnone, R. S.; Pina, I. C.; Rangel, H. R.; Dagger, F.; Suarez, A. I.; Reddy, M. V. R.; Faulkner, D. J. (1998) "Antileishmanial Cyclic Peroxides from the Palauan Sponge Plakortis aff. angulospiculatus" *Tetrahedron* 54:3057–3068.

Davidson, Bradley S. (1991) "Cytotoxic Five–Membered Cyclic Peroxides From a Plakortis Sponge" *J. Org. Chem.* 56:6722–6724.

Faulkner, D.J. (1998) *Natural Products Reports* 15:113–158.

Fontana, A.; Ishibashi, M.; Kobayashi, J. (1998) "New Polyketide Peroxides from Okinawan Marine Sponge Plakortis sp."*Tetrahedron* 54:2041–2408.

Fontana, A.; Ishibashi, M.; Shigemori, H.; Kobayashi, J. (1998) "New Cyclic Polyketide Peroxides from Okinawan Marine Sponge Plakortis sp." *J. Natl. Prod.* 61:1427–1429.

Gunasekera, S.P., M. Gunasekera, R.E. Longley and G.K. Schulte (1990) "Discodermolide: A new bioactive polyhydroxy lactone from the marine sponge Discodermia dissoluta" *J. Org. Chem.*, 55:4912–4915.

Gunasekera, S. P.; Gunasekera, M.; Gunawardana, G. P.; McCarthy, P.; Burres, N. (May 1990) "Two New Bioactive Cyclic Peroxides From The marine Sponge Plakortis angulospiculatus" *J. Nat. Prod.* 53:669–674.

Gunasekera, S.P. et al. (1991) *J. Org. Chem.* 56:1346 (Correction to, and attached with 55:4912–4915.

Harrison, Blaine and Phillip Crews (1998) "Cyclic Polyketide Peroxides and Acyclic Diol analogues from the Sponge Plakortis lita" *J. Nat. Prod.* 61:1033–1037.

Higgs, Martin D. and D. John Faulkner (1978) "Plakortin, an Antibiotic from Plakortis halichondrioides" *J. Org. Chem*, 43:3454–3457.

Horton, Paul A., Ross E. Longley, Michelle Kelly–Borges, Oliver J. McConnell (Oct. 1994) "New Cytotoxic Peroxylactones From The Marine Sponge, *Plakinastrella Onkodes*" *Journal of Natural Products* 57(10):1374–1381.

Minale, L. et al. (1976) "Natural Products from Porifera" *Fortschr. Chem. Org. Naturst.* 33:1–72.

Patil, A. D.; Freyer, A. J.; Carte, B. Johson, R. K.; Lahouratate, P. (1996) "Plakortides, Novel Cyclic Peroxides from the Sponge Plakortis halichondrioides: Activators of Cardiac SR–CA$^{2+}$ –Pumping ATPase" *J. Natl. Prod.* 59:219–223

Phillipson, D. W.; Rinehart, K. L. Jr. (1983) "Antifungal Peroxide–Containing Acids from Two Caribbean Sponges" *J. Am. Chem. Soc.* 105:7735–7736.

Qureshi, A.; Salva, J. Harper, M. K.; Faulkner, D. J. (1998) "New Cyclic Peroxides from the Philippine Sponge Plakinastrella sp." *J. Nat. Prod.* 61:1539–1542.

(List continued on next page.)

*Primary Examiner*—Ba K. Trinh
(74) *Attorney, Agent, or Firm*—Saliwanchik, Lloyd & Saliwanchik

(57) ABSTRACT

The novel compositions and methods of the subject invention can be used in antifugal applications. The antifugal agents of the subject invention can be used in the treatment of an animal or human having a fugal infection. In a further embodiment the compounds can be used to treat plant fugal infections, disinfect surfaces, and prevent spoilage of organic compositions such as food and cosmetics.

30 Claims, No Drawings

OTHER PUBLICATIONS

Rudi, Amira and Yoel Kashman (1993) "There New Cytotoxic Metabolites From The Marine Sponge *Plakortis halichondrioides*" *J. Natl. Prod.* 56:1827–1830.

Stierle, Donald B. and D. John Faulkner (1979) "Metabolites of the Marine Sponge *Chondrosia collectrix*" *J. Org. Chem.* 44:964–968.

Stierle, D. B.; Faulkner, D. J. (1980) "Metabolites of Three Marine Sponges of the Genus Plakortis" *J. Org. Chem.* 45:3396–3401.

Uemura, D., K. Takahashi, T. Yamamoto, C. Katayama, J. Tanaka, Y. Okumura, Y. Hirata (1985) "Norhalichondrin A; An Antitumor Polyether Macrolide from a Marine Sponge" *J. Am. Chem. Soc.* 107:4796–4798.

CYCLIC PEROXIDES AS NOVEL ANTIFUNGAL AGENTS

CROSS REFERENCE TO A RELATED APPLICATION

This application claims priority to provisional patent application Ser. No. 60/219,519, filed Jul. 20, 2000.

The subject invention was made with government support under a research project supported by NIH NIAID Grant No. AI40715. The government has certain rights in this invention.

BACKGROUND OF THE INVENTION

Of great importance to man is the control of fungi which can cause human, animal and plant diseases as well as food spoilage. Considerable research and resources have been devoted to identifying antifungal agents. While certain methods and chemical compositions have been developed which aid in inhibiting or controlling the growth of fungi, new methods and antifungal compositions are needed.

Only about 100 of the thousands of known species of yeasts and molds cause disease in humans or animals. Only the dermatophytes and Candida are commonly transmitted from one human to another.

Human mycotic infections may be grouped into superficial, subcutaneous, and deep (or systemic) mycoses. Superficial fungal infections of skin, hair, and nails may be chronic and resistant to treatment but rarely affect the general health of the patient. Deep mycoses, on the other hand, may produce systemic involvement and are sometimes fatal.

The deep mycoses are caused by organisms that live free in nature in soil or on decaying organic material and are frequently limited to certain geographic areas. In such areas, many people acquire the fungal infection. A majority develop only minor symptoms or none at all, and only a small minority of infections progress to full-blown serious or fatal disease. The host's cell-mediated immune reactions are of paramount importance in determining the outcome of such infections.

Pathogenic fungi generally produce no toxins. In the host, they regularly induce hypersensitivity to their chemical constituents. In systemic mycoses, the typical tissue reaction is a chronic granuloma with varying degrees of necrosis and abscess formation.

Fungal infections are common to a large number of animal species. Common agents of fungal infections include various species of the genii Candida and Aspergillus, and types thereof, as well as others. While external fungus infections can be relatively minor, systemic fungal infections can give rise to serious medical consequences. The incidence of fungal infections has undergone a significant increase, particularly in humans. This increase is, at least in part, attributable to an ever increasing number of patients having impaired immune systems, both as a result of medical therapy for other conditions, and as a result of diseases such as AIDS which compromise the immune system. Fungal disease, particularly when systemic, can be life threatening to patients having an impaired immune system. See, for example, U.S. Pat. No. 5,891,861.

A number of prior art pharmaceutical agents have been developed for the treatment of fungal diseases. These materials include compounds such as amphotericin B (AMB), triazoles and flucytosin. AMB is the drug of choice for many systemic fungal infections due to its broad range of activity; however, it is harmful to the kidneys and must be administered intravenously. Many of the triazoles exhibit broad ranging activity and can be administered orally; however, many strains of fungi have become resistant to these materials. Consequently, there is a need for a new group of agents which are effective in elminating fungus disease.

Food spoilage is typically caused by bacteria and fungi. Foods such as low-fat spreads, cheese, tea-based beverages, fruit- and tomato-based products are among the vulnerable food products. See, for example, U.S. Pat. No. 5,888,504. Although fungi can sometimes be controlled through heat treatment, an inactivating heat treatment is not always desirable or possible. Furthermore fungal spores present in factories can cause problems at the packing stage. Combating bacteria is relatively easy; fungi, however, can survive under very adverse conditions. Therefore, new compounds for preserving and protecting food are needed.

Post-harvest losses during storage of plant produce are caused, inter alia, by fungal and bacterial pathogens. Fungicidal compounds have long been used to increase yields and extend agricultural production capabilities into new areas. They have also been extremely important tools for ameliorating season-to-season differences in yield and quality caused by weather-driven variations in disease pressure.

Chemical fungicides have provided an effective method of control; however, the public has become concerned about the amount of residual chemicals which might be found in food, ground water and the environment. Stringent new restrictions on the use of chemicals and the elimination of some effective pesticides from the market place could limit economical and effective options for controlling fungi.

One example of the need to control post-harvest spoilage of agriculture products pertains to green and blue molds of citrus fruits caused by *Penicillium digitatum* and *P. italicum*. These molds cause severe damage during storage and shipping. The existing fresh-market industry relies completely on a combination of several chemical treatments to deliver sound fruit to distant markets over substantial periods of time without excessive damage caused by these molds. Unfortunately, there are increasing concerns about the safety of the chemicals currently used to control these fungal pathogens. Also, there are increasing problems with fungal strains with resistance to the most effective compounds.

In another example, powdery mildew of grapes caused by *Uncinula necator* can cause severe damage even in dry areas such as California. Traditionally this disease was controlled with applications of elemental sulfur, but this necessitates frequent, high volume applications of an irritating material. The introduction of egosterol biosynthesis inhibiting fungicides (primarily triazoles) greatly simplifies control, but also selects for tolerant strains. Some of these compounds are also known to have potential teratogenic effects and very long soil residuals. In these and other examples, alternative control methods are in great demand—particularly methods which are safer or more environmentally benign.

To prevent fungal spoilage it is common practice in many countries to spray produce with systemic fungicides in the field and to dip harvested produce in fungicide solutions prior to storage. Since the oncogenic nature of many of the most commonly used fungicides is increasingly recognized and because the persistence of most fungicides is increased by the low storage temperatures the postharvest use of fungicides is of growing concern.

Additionally, resistance to the fungicides, used has been reported and suppression of the main spoilage organism *B. cinera* by fungicides such as BENOMYL fungicide has been shown to result in increased population of *A. brassicicola* which causes a more penetrating rot of produce than *B. cinera*. See, for example, U.S. Pat. No. 5,869,038.

The future role of fungicides in agriculture is increasingly threatened by several factors including; the development of pest resistance, increasing concerns about food safety, and environmental accumulation of toxic compounds. As older fungicides are removed from the market due to regulatory changes there is an increasing need to find new effective fungicidal compounds.

In searching for new biologically active compounds, it has been found that some natural products and organisms are potential sources for chemical molecules having useful biological activity of great diversity. For example, the diterpene commonly known as taxol, isolated from several species of yew trees, is a mitotic spindle poison that stabilizes microtubules and inhibits their depolymerization to free tubulin (Fuchs, D. A., R. K. Johnson [1978] *Cancer Treat. Rep.* 62:1219–1222; Schiff, P. B., J. Fant, S. B. Horwitz [1979] *Nature* (London) 22:665–667). Taxol is also known to have antitumor activity and has undergone a number of clinical trials which have shown it to be effective in the treatment of a wide range of cancers (Rowinski, E. K. R. C. Donehower [1995] *N. Engl. J. Med.* 332:1004–1014). See also, e.g., U.S. Pat. Nos. 5,157,049; 4,960,790; and 4,206,221.

Marine sponges have also proven to be a source of biologically active chemical molecules. A number of publications disclose organic compounds derived from marine sponges including Scheuer, P. J. (ed.) *Marine Natural Products, Chemical and Biological Perspectives*, Academic Press, New York, 1978–1983, Vol. I–V; Uemura, D., K. Takahashi, T. Yamamoto, C. Katayama, J. Tanaka, Y. Okumura, Y. Hirata (1985) *J. Am. Chem. Soc.* 107:4796–4798; Minale, L. et al. (1976) *Fortschr. Chem. org. Naturst.* 33:1–72; Faulkner, D. J. (1998) *Natural Products Reports* 15:113–158; Gunasekera, S. P., M. Gunasekera, R. E. Longley and G. K. Schulte (1990) "Discodermolide: A new bioactive polyhydroxy lactone from the marine sponge *Discodermia dissoluta*" *J. Org. Chem.*, 55:4912–4915; (1991) *J. Org. Chem.* 56:1346; U.S. Pat. No. 4,808,590 discloses compounds, having antiviral, antitumor, and antifungal properties, isolated from the marine sponge Theonella sp. New antiviral, antitumor and antifungal compositions and their methods of use are described in U.S. Pat. Nos. 4,801,606; 4,808,590, T. Higa, S. Sakemi and S. Cross. Also, the isolation and elucidation of spongistatins 1–7 are described in U.S. Pat. Nos. 5,328,929; 5,393,897; and 5,436, 400. These compounds have been found to have antitumor and antifungal properties. See, U.S. Pat. No. 5,883,120.

Other natural products of marine origin include the following:

1. Plakinic acid A

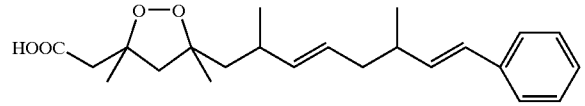

Source: unnamed sponge of the family Plakinidae from Caribbean
Reference: Phillipson, D. W.; Rinehart, K. L. Jr. *J. Am. Chem. Soc.* 1983, 105, 7735–7736.
Antifungal activity: 24 mm vs. *S. cerevisiae* and 25 mm vs. *P. atrovenetum* at 100 mg/disk 2. Plakinic acids C and D and epi-plakinic acid C and D

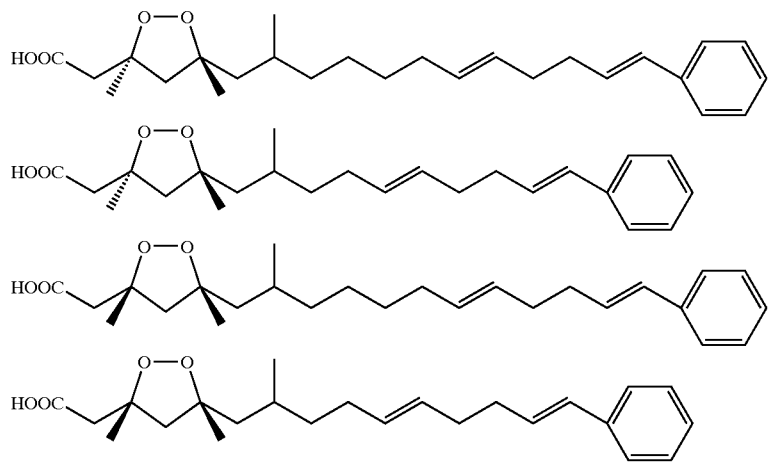

Source: Plakortis sp. collected in the Fiji Islands
Reference: Davidson, B. S. *J. Org. Chem.* 1991, 56, 6722–6724.
Cytotoxicity: against human epidermoid carcinoma (KB) cells, human colorectal adenocarcinoma (LoVo) cells, and L1210 murine leukemia cells.

3. Epiplakinic acid E methyl ester

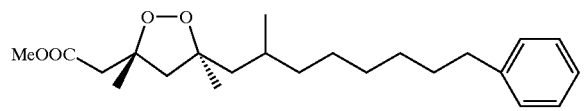

Source: *Plakinastrella onkodes* collected in the Gulf of Mexico
Reference: Horton, P. A.; Longley, R. E.; Kelly-Borges, M.; McConnell, O. J.; Ballas, L. M. *J. Nat. Prod.* 1994, 57, 1374–1381.
Cytotoxicity: against human lung carcinoma (A549) and murine leukemia (P388) cells.

4. (3R,5S,12E,14E,17Z)-3,5-dimethyl-3,5-peroxydodeca-12,14,17-trienoate and methyl ester

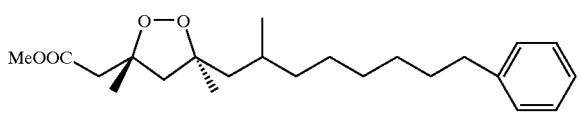

Source: Plakinastrella sp. collected at Hagakhak Island, Philippines

Reference: Qureshi, A.; Salva, J. Harper, M. K.; Faulkner, D. J. *J. Nat. Prod.* 1998, 61, 1539–1542.

Essentially inactive against *Candida albicans*

5. Natural and unnatural 1,2-dioxolane carboxylate analogues

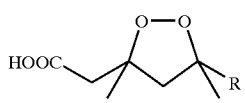

$R=C_{13}H_{27}$
$R=C_{14}H_{29}$
$R=C_{15}H_{31}$
$R=C_{16}H_{33}$
$R=C_{17}H_{35}$

Source: isolated from Halichondriidae sponges or prepared by synthesis

Reference: Patil, A. D. U.S. Pat. No. 4,879,307 (1989); C. A., 1988, 109, 17027f.

Reference: Bloodworth, A. J.; Bothwell, B. D.; Collins, A. N.; Maidwell, N. L. *Tetrahedron Let.* 1996, 37, 1885–1888. (Synthesis)

Activity: Active against tumor cell lines

6. Plakortin and its free acid; 3-Epiplakortin; 9,10-dihydro-3-epiplakortin; and other related skeleton peroxides

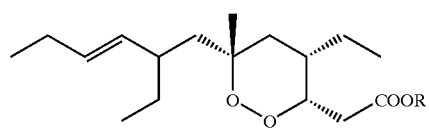

R=Me
R=H

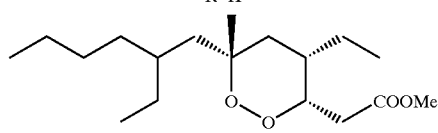

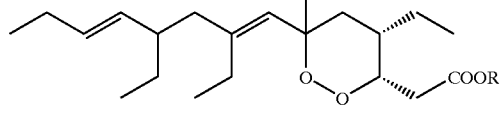

R=Me
R=H

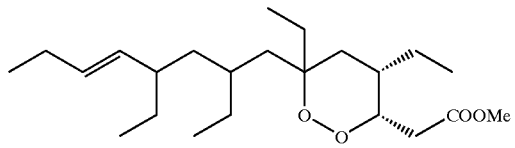

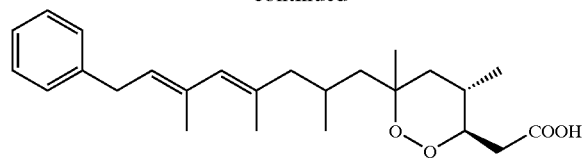

Source: Caribbean sponge *Plakortis halichondrioides* and/or *Plakortis zyggompha*

Reference: Higgs, M. D.; Faulkner, D. J. *J. Org. Chem.* 1978, 43, 3454–3457.

Reference: Stierle, D. B.; Faulkner, D. J. *J. Org. Chem.* 1979, 44, 964–968.

Reference: Stierle, D. B.; Faulkner, D. J. *J. Org. Chem.* 1980, 45, 3396–4301.

Reference: Phillipson, D. W.; Rinehart, K. L. Jr. *J. Am. Chem. Soc.* 1983, 105, 7735–7736.

Activity: plakortin was essentially bioinactive, the free acid was shown to inhibit *S. cerevisiae, P. atrovenetum* and *B. subtilis*. The activity of the other compounds was not reported.

7. Two epimeric peroxy acids and their esters

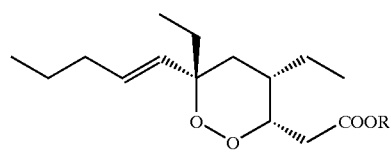

R=Me
R=H

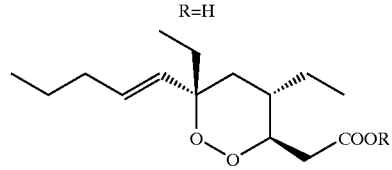

R=Me
R=H

Source: Carribbean sponge *Chondrosia collectrix*

Reference: Stierle, D. B.; Faulkner, D. J. *J. Org. Chem.* 1979, 44, 964–968.

Activity: Four compounds were reported as having mild antibacterial activity

8. Plakinic acid B

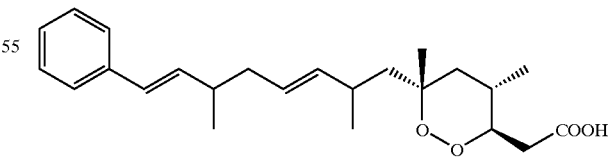

Source: unnamed sponge of the family Plakinidae from the Caribbean

Reference: Phillipson, D. W.; Rinehart, K. L. Jr. *J. Am. Chem. Soc.* 1983, 105, 7735–7736.

Activity: 20 mm vs. *S. cerevisine* and 18 mm vs. *P. atrovenetum* at 100 mg/disk 9. Unsaturated cyclic-peroxide-containing acids

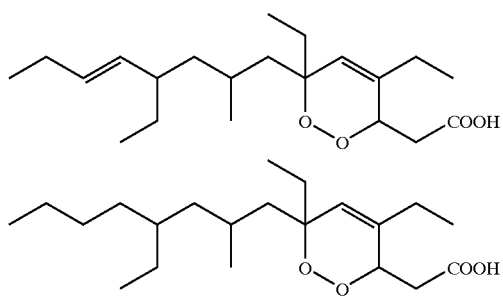

Source: *Plakortis angulospiculatus* collected off the coast of Venezuela
Reference: Gunasekera, S. P.; Gunasekera, M.; Gunawardana, G. P.; McCarthy, P.; Burres, N. *J. Nat. Prod.* 1990, 53, 669–674.
Activity: 1.6 mg/ml against *Candida albicans*, and were also active against *Aspergillus nidulans* and *Bacillus subtilis*. Cytotoxicity gave $IC_{50}$'s of 0.2–0.9 mg/ml against P388 cells.

10. Cyclic-peroxide-containing acid

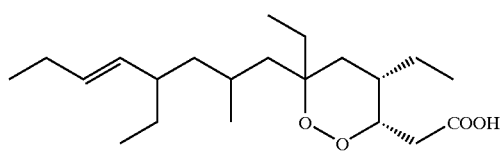

Source: *Plakortis halichondrioides* collected off the coast of Jamaica
Reference: Rudi, A.; Kashman, Y. *J. Nat. Prod.* 1993, 56, 1827–1830.
Activity: displayed an $IC_{50}$ value against P388 murine leukemia of 0.5 mg/ml.

11. Plakortide F, G, H

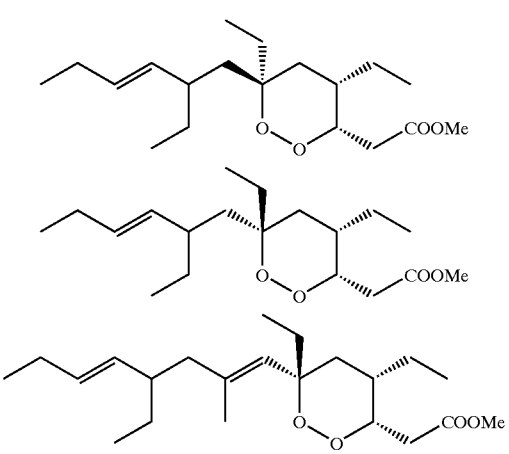

Source: *Plakortis halichondrioides* collector in Jamaica
Reference: Patil, A. D.; Freyer, A. J.; Carte, B. Johson, R. K.; Lahouratate, P. *J. Nat. Prod.* 1996, 59, 219–223.
Activity: significantly enhanced $Ca^{2+}$ uptake by the cardiac sarcoplasmic reticulum.

12. Cyclic polyketide peroxides

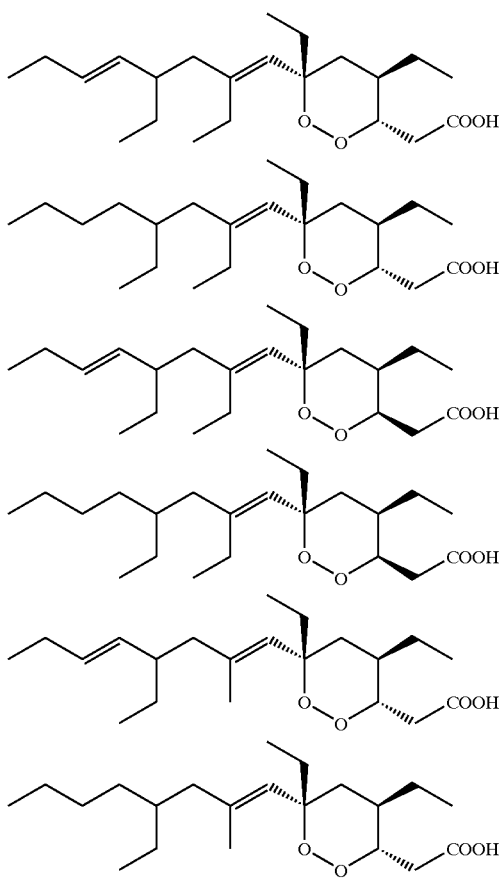

Source: Okinawan *Plakortis* sp.
Reference: Fontana, A.; Ishibashi, M.; Kobayashi, J. Tetrahedron. 1998, 54, 2041–2048.
Reference: Fontana, A.; Ishibashi, M.; Shigemori, H.; Kobayashi, J. *J. Nat. Prod.* 1998, 61, 1427–1429.
Activity: Cytotoxicity against human epidermoid carcinoma KB and murine lymphoma L1210 cells was reported.

13. Cyclic peroxides

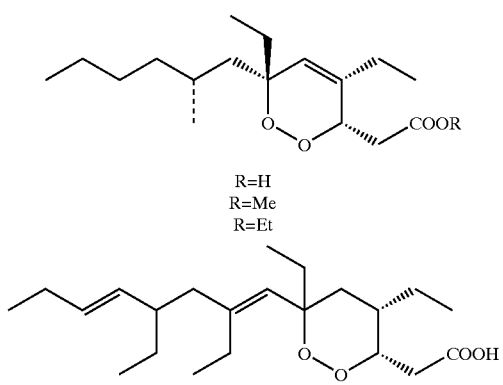

Source: Palauan sponge of *Plakortis* aff. *angulospiculatus*
Reference: Compagnone, R. S.; Pina, I. C.; Rangel, H. R.; Dagger, F.; Suarez, A. I.; Reddy, M. V. R.; Faulkner, D. J. *Tetrahedron*, 1998, 54, 3057–3068.

Activity: showed in vitro antiproliferative effects on promastigotes of *Leishmania mexicana*, a flagellate protozoan that causes leishmaniasis.

14. Polyketide peroxide

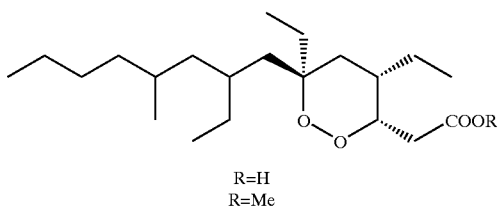

R=H
R=Me

Source: Plakortis sp. collected on the west rim of St. Francis Atoll, Amirante Islands
Reference: Braekman, J. C.; Daloze, D.; Groote, S. D.; Fernandes, J. B.; Van Soest, R. W. M. *J. Nat. Prod.* 1998, 61, 1038–1042.
Activity: exhibited toxicity toward Artemia larvae (LD50 15 mg/L).

15. Cyclic polyketide peroxides

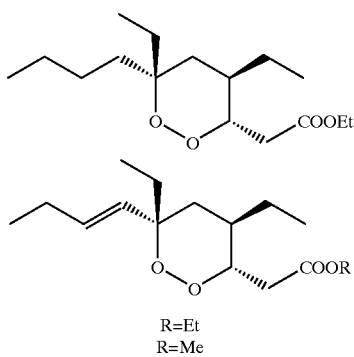

R=Et
R=Me

Source: *Plakortis lita* from Papua New Guinea
Ref: Harrison, B.; Crews, P. *J. Nat. Prod.* 1998, 61, 1033–1037.
Activity: activity in vitro against solid tumor and L1210 leukemia cell lines was reported.

Also, U.S. Pat. No. 4,731,377 describes cyclic peroxides having antitumor properties.

BRIEF SUMMARY OF THE INVENTION

A principal object of the subject invention is the provision of novel compositions of biologically active compounds. These compounds have been found to have antifungal activity. Because of this antifungal activity, the compounds of the subject invention can advantageously be used for control of unwanted fungi such as those which cause human, animal and plant disease, and those that cause spoilage of food, cosmetics, and other consumer items.

Specifically exemplified herein are six compounds (Compounds 1–6), shown below, which have been found to possess antifungal activity. The compounds of the subject invention have a cyclic peroxide functionality forming either a six or a five membered ring. The compounds also have a free carboxylic acid moiety adjacent to the peroxide-containing ring.

Compound 1

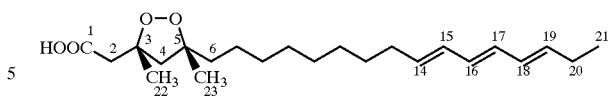

Compound 2

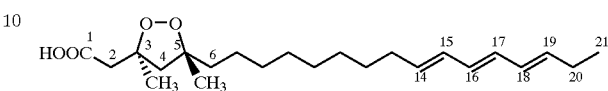

Compound 3

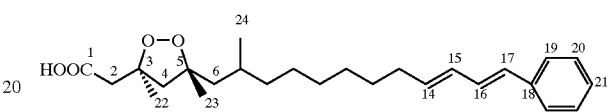

Compound 4

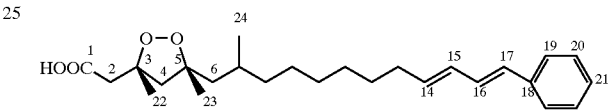

Compound 5

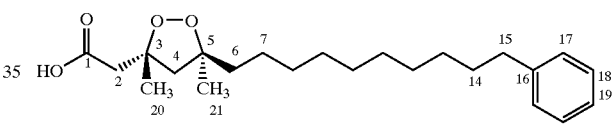

Compound 6

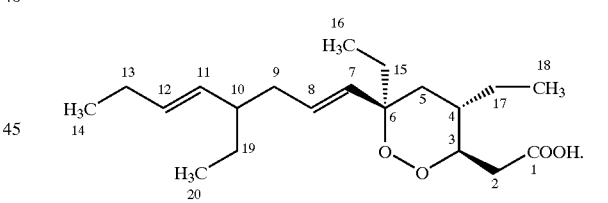

The structures of 1–4 and 6 have not been previously disclosed, while the structure of 5 has been disclosed (Longley, NMHCC Conference on Natural Products Drug Discovery, Nov. 12–14, 1997, Baltimore, Md.), but not as an antifungal agent.

Compounds 1–4 are significantly different from previously reported compounds. Compound 5 has been reported previously as an inhibitor of the enzyme cdc25a, but has not been reported to have antifungal activity.

All of the compounds have utility as antifungal agents. As such the compounds of the subject invention can be used as pharmaceutical agents to treat fungal infections in humans or animals. The compounds can also be used as disinfectants, food preservatives, and to treat plant diseases caused by fungi.

In accordance with the subject invention, methods for inhibiting fungi in a host include contacting the fungi with an effective amount of the compositions of the subject invention.

Additional aspects of the invention include the provision of methods for producing the new compounds and compositions.

Other objects and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

DETAILED DISCLOSURE OF THE INVENTION

The subject invention provides novel biologically active compounds which are useful as antifungal agents. Because of the biological activity of these compounds, they can be used for treatment of plant and animal fungal infections, to prevent spoilage of organic compositions such as food and cosmetics, and as disinfectants. In a preferred embodiment, the novel compounds, compositions and methods of use of the subject invention can advantageously be used to inhibit the growth of fungi in a mammalian host.

As used herein, reference to "antifungal activity" includes fungicidal and fungistatic activity as well as the inhibition of fungal germination or growth.

Specifically exemplified herein are compounds 1 through 6. The subject invention also concerns various salts, analogs and derivatives of these compounds.

Compounds 1 and 2 have an unprecedented triene moiety. Compounds 3 and 4 differ from the known plakinic acids in that both of the olefinic bonds are conjugated with the aromatic ring. In the previously known compounds, only one olefinic bond is conjugated with the aromatic ring. Compound 5 differs from the known plakinic acids in lacking the methyl substituent that is typically found at C-7 (on the β-carbon to the peroxide ring). No antifungal properties have been reported for the related compounds, plakinic acids c and d or epiplakinic acids c and d.

Compounds of the invention can be isolated by various fractionation and chromatographic techniques from marine sponge extracts. Isolation procedures include various chromatography techniques, e.g., column chromatography, HPLC, countercurrent chromatography with suitable columns, including multi-layer planetary coil columns. A variety of solvents are available for use as single or mixed eluents, such as methylene chloride, methanol, ethyl acetate, acetonitrile, n-propanol, n-butanol, water, and equivalent solvents. Further purifications using such procedures may also be carried out on the recovered extractions. Preferred isolation techniques for further purification include chromatographic operations such as high-pressure liquid chromatography with suitable columns with suitable solvent, particularly, acetonitrile/water, methanol/water or methanol/isopropanol/water mixtures.

Skilled chemists having the benefit of the instant disclosure, can readily use procedures to prepare the subject compounds. In carrying out such operations, suitable filtration, chromatographic and other purification techniques can be used. These techniques could include, for example, reversed phase (RPLC), column, vacuum flash, medium pressure (MPLC) and high performance liquid chromatography (HPLC) with a suitable column such as silica gel, Sephadex LH-20, ammonia-treated silica gel, bonded phase RP-18, RP-8 and amino columns. Such columns are eluted with suitable solvents as discussed above.

With a knowledge of the compounds of the subject invention, and their structures, skilled chemists can use known procedures to synthesize these compounds from available substrates.

In further embodiments of the subject invention, salts within the scope of the invention are made by adding mineral acids, e.g., HCl, $H_2SO_4$, or strong organic acids, e.g., formic, oxalic, in appropriate amounts to form the acid addition salt of the parent compound or its derivative. Thus, the compounds of the subject invention include the salts of the exemplified structures. These salts may be, for example, the sodium, potassium, and calcium salts. Also, synthesis type reactions may be used pursuant to known procedures to add or modify various groups in the preferred compounds to produce other compounds within the scope of the invention.

The scope of the invention is not limited by the specific examples and suggested procedures and uses related herein since modifications can be made within such scope from the information provided by this specification to those skilled in the art.

The subject invention pertains also to analogs and derivatives of the exemplified compounds and to the use of these analogs and derivatives as antifungal agents. As used herein, the terms "analogs" and "derivatives" refer to compounds which are substantially the same as another compound but which may have been modified by, for example, adding additional side groups.

The compounds of the subject invention are effective antifungal agents when they are simply applied to a surface, such as on the leaves or fruit of a plant or a surface to be disinfected. To facilitate this application, the compounds may be mixed with an appropriate liquid or powder agricultural carrier. Suitable liquid diluents or carriers for use in the conduct of this invention include water, petroleum distillates, or other liquid carriers, with or without various dissolved salts and surface active emulsifying and dispersing agents. These liquid compositions may be prepared by dissolving or dispersing a fungicidal amount of a compound in the appropriate compatible diluent or carrier.

Solid compositions may be prepared by dispersing the desired compounds in or on an appropriately divided carrier such as clay, talc, bentonite, diatomaceous earth, fuller's earth, and the like. When such formulations are used as wettable powders, biologically compatible dispersing agents such as liquosulfonates and various non-ionic, anionic, amphoteric, or cationic dispersing and emulsifying agents can be used.

The compositions of the subject invention can be used in the treatment of one or more fungal infections, such as Aspergillosis, Candidiasis or thrush, internal infections such as cryptococcosis, epidermal infections, infections caused by antibiotic resistant fungi and the like. Similar fungal infections are enumerated in the AMA Home Medical Encyclopedia published by Random House, Inc. 1989.

The dosage administered will be dependent upon the identity of the fungus; the location of the fungal infection; the type of host involved; the nature of concurrent treatment, if any; and the frequency of treatment specified.

Illustratively, dosage levels of the administered active ingredients are: intravenous, 0.1 to about 200 $\mu$g/kg; orally, 5 to about 100 $\mu$g/kg of host body weight.

Expressed in terms of concentration, an active ingredient can be present in the compositions of the present invention for localized use about the cutis, intranasally, pharyngolaryngeally, bronchially, intravaginally, or ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in salves and ointments for topical application although unit dosage forms, such as tablets, capsules, pills, powders, suppositories, sterile parenteral solutions or suspensions, sterile non-parenteral solutions or suspensions, lozenges and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as an adjuvant to the filling operation, a lubricant such as talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil The lubricated mixture is then compressed into tablets.

Advantageously, the tablet can be provided with a protective coating consisting of a sealing coat or enteric coat of shellac, a coating of sugar and methylcellulose and polish coating of carnauba wax.

Fluid unit dosage forms for oral administration such as in syrups, elixirs and suspensions can be prepared wherein each teaspoonful of composition contains a predetermined amount of an active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the active ingredient can be dissolved in a suitable vehicle for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or exposure to ethylene oxide before suspending in the sterile vehicle. Advantageously, a surfactant or wetting agent is included in the composition to faciliate uniform distribution of the active ingredient.

In addition to oral and parenteral administration, the vaginal routes can be utilized by means of a suppository. A vehicle which has a melting point at about body temperature or one that is readily soluble can be utilized. For example, cocoa butter and various polyethylene glycols (Carbowaxes) can serve as the vehicle.

For use as aerosols, the active ingredients can be packaged in a pressurized aerosol container together with a gaseous or liquified propellant, for example, dichlorodifluoromethane, carbon dioxide, nitrogen, propane, and the like, with the usual adjuvants such as cosolvents and wetting agents, as may be necessary or desirable.

In the treatment of dermatological fungi, the active ingredient will be delivered to the site as an ointment or salve which will comprise water and oil emulsion as the principal carrier. Other conventional ingredients, when conditions and aesthetics dictate, include petrolatum and mineral oil, lipophilic solubilizers such as polyethylene glycol, carbowax, moisturizers such as lanolin and fragrance.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonful, dropperfuls, ampules, vials, segregated multiples of any of the foregoing, and other forms as herein described.

The active ingredients to be employed as antifungal agents can be easily prepared in such unit dosage form with the employment of pharmaceutical materials which themselves are available in the art and can be prepared by established procedures. For a discussion of formulations see, for example, U.S. Pat. No. 5,883,120.

Materials and Methods

Preparation of Stock Cultures of *Aspergillus fumigatus*. Freeze-dried *A. fumigatus* stocks (ATCC 16424) were resuspended in 1 mL sterile distilled, de-ionized water. Slants were made with five mL of MPG agar (2% (w/v) malt extract, 2% (w/v) glucose, 0.1% (w/v) bacto-peptone, 1.5% (w/v) agar) in 16×125 mm disposable glass culture tubes, inoculated with approximately 50 $\mu$L of the above cell suspension, incubated at 25° C. for 7 days and then frozen at −80° C. To prepare glycerol stocks, a slant was thawed and conidia were resuspended in 5 mL sterile distilled, de-ionized water. Two hundred mL of MPG agar (2% (w/v) malt extract, 2% (w/v) glucose, 0.1% (w/v) bacto-peptone, 1.5% (w/v) agar) in a 1000 mL Ehrlenmeyer flask were inoculated with this 5 mL cell suspension, incubated 5–7 days at 37° C., and then frozen at −20° C. This flask was thawed and conidia were resuspended in 20 mL of sterile distilled, de-ionized water. Sufficient glycerol was added to this 20 mL suspension to make a 10% (v/v) solution (final concentration). This solution was aliquoted in 1 mL portions, frozen on dry ice, and stored at −50° C. A thawed glycerol stock was used to inoculate 96-well microtiter plates at $2 \times 10^4$ conidia per 200 μL per well in liquid RPMI medium (RPMI-1640 [Gibco], 0.165 M MOPS, pH 7.0).

Preparation of Stocks Cultures of Candida albicans. Freeze-dried C. albicans yeast stocks (ATCC 90028) were each resuspended in 1 mL sterile distilled, de-ionized water. Slants were made with five mL of MPG agar (2% (w/v) malt extract, 2% (w/v) glucose, 0.1% (w/v) bacto-peptone, 1.5% (w/v) agar) in 16×125 mm disposable glass culture tubes, inoculated with approximately 50 mL of the above cell suspension, incubated at 25° C. for 7 days and then frozen at −80° C. To prepare glycerol stocks, a slant was thawed and the yeast cells were resuspended in 5 mL sterile distilled, de-ionized water. This 5 mL cell suspension was used to inoculate 50 mL of Sabouraud Dextrose Broth (3% (w/v) [Gibco]) in a 250 mL Ehrlenmeyer flask and was incubated 18–24 hours at 37° C., 180 rpm. Fifty milliliters of Sabouraud Dextrose Broth in a 250 mL Ehrlenmeyer flask were inoculated with $1 \times 10^7$ cells per mL of the previous culture and grown under the same conditions. After 18–24 hours, sufficient glycerol was added to this culture to make a 10% (v/v) solution (final concentration). This solution was aliquoted in 1 mL portions, frozen on dry ice, and stored at −50° C. A thawed glycerol stock was used to inoculate 50 mL Sabouraud's Dextrose Broth in a 250 mL Ehrlenmeyer flask and grown for 18–24 hours, at 37° C., 180 rpm. This culture was used to inoculate 96-well microtiter plates [Nunc] at $2 \times 10^3$ cells per 200 μL per well in liquid RPMI medium (RPMI-1640 [Gibco], 0.165 M MOPS, pH 7.0).

Following are examples which illustrate procedures for practicing the invention. These examples should not be construed as limiting. All percentages are by weight and all solvent mixture proportions are by volume unless otherwise noted.

EXAMPLE 1

Purification and Structural Data for Compounds 1 and 2

Collection of Sponge Material. The sponge was collected at a depth of 25 ft in the Seychelles on the west coast of Felicite Island (latitude 04°19.28S, longitude 55°51.95E), frozen immediately after collection, and kept frozen until used.

Taxonomy of Source Organism. The sponge is identified as Plakinastrella sp.(Class Demospongiae, Order Homosclerophorida, Family Plakinidae) (Diaz and Van Soest, 1994). The sponge was thickly encrusting, lobate, with a row of oscules, 4 mm in diameter, on a ridge at the top of the sponge. Color in life was dark brown externally and tan internally. The consistency was firm. Spicules are calthrops and diods in at least three size categories. This description most closely matches Plakinastrella onkodes from the Caribbean (Zea, 1987), but it is likely to be a new species. A taxonomic reference specimen is deposited at the Harbor Branch Oceanographic Museum (HBOM catalog number 003:00958), sample number 15-VI-90-3-003).

Purification of Compounds. The frozen sponge (103 g wet wt) was diced and extracted with EtOH (5×200 mL). The combined EtOH extracts were concentrated to dryness (3.15 g) and partitioned between 1:1 n-BuOH/$H_2O$. The n-BuOH partition was concentrated to dryness (0.73 g) and was further purified via vacuum flash column chromatography on a Si gel (Kieselgel 60H) stationary phase using a step gradient of heptane and heptane/EtOAc as eluent. The fractionation was monitored by antifungal assay against C. albicans. The antifungal active fractions which eluted with 80% EtOAc and 100% EtOAc were further separated by HPLC on a Si gel HPLC column (Whatman Partisil 10, 10×500 mm) eluted with 1% MeOH in $CH_2Cl_2$ to yield a mixture of compounds 1, and 2. The mixture was further purified using reversed-phase HPLC (Vydac Protein and Peptide C18 column, 10×250 mm, Solvent A: 50% methanol in water v/v; Solvent B: 100% isopropanol; t=0 A:B 80:20; t=30 A:B 0:100; t=35 A:B 0:100; flow=3 ml/min; compounds detected by UV absorption at 280 nm.) This yielded pure acids 1 (1.2, mg, retention time: 19.91 minutes) and 2 (1.1 mg, retention time: 21.50 minutes).

Compound 1

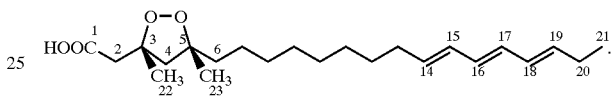

Structural Data for Compound 1:

$^1$H NMR (CDCl$_3$): δ 6.07 (2H, m, H-16, 17), 6.02 (2H, m, H-15, 18), 5.69 (1H, dt, J=7.3, 14.5 Hz, H-19), 5.63 (1H, dt, J=7.2, 14.1 Hz, H-14), 2.73 (2H, s, H-2), 2.48 (1H, d, J=12.5 Hz, H-4a), 2.14 (1H, d, J=12.5 Hz, H-4b), 2.10 (2H, q, J=7.3 Hz, H-20), 2.06 (2H, q, J=7.2 Hz, H-13), 1.55 (m, H-6a), 1.47 (3H, s, H-22), 1.37 (m, H-12), 1.36 (3H, s, H-23), 1.26 (m, H-6b, 7, 8, 9, 10, 11).

$^{13}$C NMR (CDCl$_3$): δ 171.94 (s, C-1), 135.93 (d, C-19), 134.42 (d, C-14), 130.49 (d, C-15), 130.88 (d, C-16), 130.88 (d, C-17), 129.52 (d, C-18), 86.96 (s, C-5), 83.78 (s, C-3), 55.56 (t, C-4), 43.62 (t, C-2), 38.72 (t, C-6), 32.79 (t, C-13), 30.02 (t, C-11), 29.70 (t, C-8), 29.39 (t, C-12), 29.38 (t, C-9), 29.14 (t, C-10), 25.81 (t, C-20), 24.83 (q, C-23), 23.61 (q, C-22), 13.61 (q, C-21).

IR (CHCl$_3$): 2925, 2853, 1709, 1460, 1375, 1305, 1210, 994, 796 cm$^{-1}$.

HRFABMS: m/z 401.2636 for $C_{23}H_{38}O_4Na$ [M+Na]$^+$ (calculated 401.2668).1

Compound 2

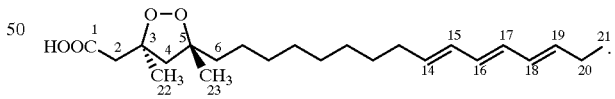

Structural Data for Compound 2:

$^1$H NMR (CDCl$_3$): δ 6.06 (2H, m, H-16, 17), 6.02 (2H, m, H-15, 18), 5.68 (1H, dt, J=7.2, 14.4 Hz, H-19), 5.63 (1H, dt, J=7.2, 14.1 Hz, H-14), 2.75 (2H, s, H-2), 2.40 (1H, d, J=12.5 Hz, H-4a), 2.25 (1H, d, J=12.5 Hz, H-4b), 2.08 (2H, q, J=7.2 Hz, H-20), 2.05 (2H, q, J=7.2 Hz, H-13), 1.65 (m, H-6a), 1.45 (3H, s, H-22), 1.39 (m, H-12), 1.28 (3H, s, H-23), 1.28 (m, H-6b), 1.16–1.53 (m, H-7, 8, 9, 10, 11).

$^{13}$C NMR (CDCl$_3$): δ 171.80 (s, C-1), 135.90 (d, C-19), 134.41 (d, C-14), 130.48 (d, C-15), 130.83 (d, C-16), 130.87 (d, C-17), 129.51 (d, C-18), 86.86 (s, C-5), 83.68 (s, C-3), 55.51 (t, C-4), 43.94 (t, C-2), 38.77 (t, C-6), 32.78 (t, C-13), 30.02 (t, C-11), 29.70 (t, C-8), 29.70 (t, C-12), 29.42 (t, C-9), 29.14 (t, C-10), 25.81 (t, C-20), 24.75 (q, C-22), 23.69 (q, C-23), 14.11 (q, C-21).

IR (CHCl$_3$): 2928, 2857, 1715, 1463, 1376, 1210, 993 cm$^{-1}$.

HRFABMS: m/z 379.22816 for C$_{23}$H$_{39}$O$_4$ [M+H]$^+$ (calculated 379.2850).

EXAMPLE 2

Purification and Structural Data for Compounds 3 and 4

Collection of Sponge Material. The sponge was collected at a depth of 217 feet in the US Gulf of Mexico, 0.75 nautical miles SW of Sanibel Island, Fla. (latitude 26°18.096'N., longitude 83°34.682'W). It was frozen immediately after collection, and kept frozen until used.

Taxonomy of Source Organism. The sponge is identified as *Plakinastrella onkodes* (Class Demospongiae, Order Homosclerophorida, Family Plakinidae) (Zea, 1987; Diaz and Van Soest, 1994). The sponge was a cluster of lobes with apical oscules. Color in life was grey externally and tan internally. The consistency was firm. Spicules are calthrops and diods in at least three size categories. A taxonomic reference specimen is deposited at the Harbor Branch Oceanographic Museum (HBOM catalog number 003:00967), sample number 10-VIII-95-3-004).

Purification of Compounds. The sample (50 g wet wt) was diced and extracted with EtOH (5×200 mL). The crude extracts were concentrated to dryness (2.76 g) and partitioned between 1:1 EtOAc/H$_2$O. The EtOAc partition was concentrated to dryness (262.6 mg) and was further purified via vacuum flash column chromatography on a Si gel (Kieselgel 60H) stationary phase using a step gradient of heptane and heptane/EtOAc as eluent. The fraction 5 (6.8 mg) which eluted with 60% EtOAc were further purified by reversed-phase HPLC (Vydac Protein and Peptide C18 column, 10×250 mm, Solvent A: 5% acetonitrile in water v/v; Solvent B: 100% acetonitrile; t=0 A:B 80:20; t=20, A:B 0:100; t=30 A:B 0:100; flow=3 ml/min; Detected by uv absorption observed at 254 nm.), 1.6 mg compound 3 (retention time=23.83 minutes) was yielded. Fraction 4 (9.6 mg) which eluted with 50% EtOAc was further purified by reversed-phase HPLC [Vydac Protein and Peptide C18 column, 10×250 mm, Solvent A: 5% acetonitrile in water v/v; Solvent B: 100% acetonitrile; t=0 minutes A:B 80:20; t=15 A:B 80:20; t=25, A:B 0:100; t=30 A:B 0:100; flow=3 ml/min; Detected by UV absorption observed at 254 nm.), 0.8 mg of compound 4 (retention time=15.33 minutes) was obtained.

Compound 3

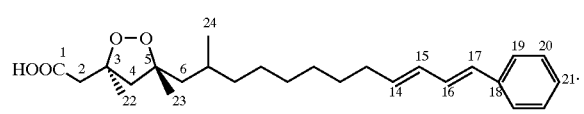

$^1$H NMR (CDCl$_3$): δ 7.35 (d, J=7.8 Hz, H-19), 7.27 (t, J=7.5 Hz, H-20), 7.16 (t, J=7 Hz, H-21), 6.72 (1H, dd, J=10, 15.5 Hz, H-16), 6.42 (1H, d, J=15.5 Hz, H-17), 6.18 (1H, dd, J=10, 15 Hz, H-15), 5.81 (1H, dt, J=7, 15 Hz, H-14), 2.73 (2H, s, H-2), 2.45 (1H, d, J=12.5 Hz, H-4a), 2.21 (1H, d, J=12.5 Hz, H-4b), 1.60 (m, H-6), 1.58 (m, H-7), 1.45 (3H, s, H-22), 1.40 (m, H-12), 1.31 (3H, s, H-23), 1.25 (m, H-8a, 9, 10, 11), 1.14 (m, H-8b), 0.93 (3H, t, J=6.2 Hz, H-24).

$^{13}$C NMR (CDCl$_3$): δ 173.16 (s, C-1), 137.71 (s, C-18), 135.95 (s, C-14), 130.54 (d, C-15), 129.96 (d, C-16), 129.48 (d, C-17), 128.55 (d, C-20), 127.08 (d, C-21), 126.13 (d, C-19), 87.07 (s, C-5), 83.61 (s, C-3), 57.34 (t, C-4), 46.44 (d, C-6), 43.58 (t, C-2), 38.62 (t, C-8), 32.86 (t, C-13), 29.74 (t, C-12), 29.59 (t, C-7), 29.32 (t, C-11), 29.25 (t, C-10), 27.03 (t, C-9), 23.87 (q, C-22), 23.35 (q, C-23), 20.99 (q, C-24).

IR (CHCl$_3$): 2930, 2853, 1716, 1702, 1684, 1654, 1635, 1559, 1539, 1507, 1457, 1419, 1374, 1204, 972, 670 cm$^-$.

Compound 4

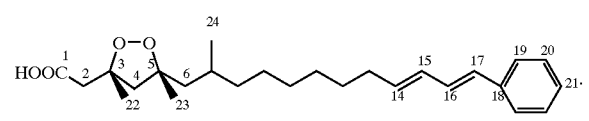

$^1$H NMR (CDCl$_3$): δ 7.35 (d, J=7.8 Hz, H-19), 7.27 (t, J=7.5 Hz, H-20), 7.16 (t, J=7 Hz, H-21),6.73 (1H, dd, J=10, 15.5 Hz, H-16), 6.42 (1H, d, J=15.5 Hz, H-17), 6.18 (1H, dd, J=10, 15 Hz, H-15), 5.80 (1H, dt, J=7, 15 Hz, H-14), 2.72 (2H, s, H-2), 2.46 (1H, d, J=12.5 Hz, H-4a), 2.20 (1H, d, J=12.5 Hz, H-4b), 1.64 (m, H-6), 1.60 (m, H-7), 1.46 (3H, s, H-22), 1.40 (m, H-12), 1.35 (3H, s, H-23), 1.26 (m, H-8a, 9, 10, 11), 1.14 (m, H-8b), 0.90 (3H, t, J=6.2 Hz, H-24).

$^{13}$C NMR (CDCl$_3$): δ 171.99 (s, C-1), 137.70 (s, C-18), 135.95 (s, C-14), 130.55 (d, C-15), 129.98 (d, C-16), 129.48 (d, C-17), 128.56 (d, C-20), 127.09 (d, C-21), 126.13 (d, C-19), 87.34 (s, C-5), 83.79 (s, C-3), 57.43 (t, C-4), 45.94 (d, C-6), 43.79 (t, C-2), 38.15 (t, C-8), 32.86 (t, C-13), 29.72 (t, C-12), 29.57 (t, C-7), 29.31 (t, C-11), 29.24 (t, C-10), 27.00 (t, C-9), 24.63 (q, C-23), 23.49 (q, C-22), 20.87 (q, C-24).

IR (CHCl$_3$): 2932, 2853, 1716, 1698, 1682, 1652, 1646, 1576, 1558, 1540, 1507, 1457, 1418, 1395, 1204, 972, 670 cm$^-$.

EXAMPLE 4

Purification and Structural Data for Compound 5, Epiplakinic Acid h

Collection of Sponge Material. The sponge was collected at a depth of 934 feet off the North coast of Mayaguana, Bahamas, (latitude 22°26.807'N, longitude 73°02.338'W). It was frozen immediately after collection, and kept frozen until used.

Taxonomy of Source Organism. The sample consists of two species, Strongylophora sp. (Class Demospongiae, Order Haplosclerida, Family Petrosiidae) (Van Soest, R. W. M. [1980] "Marine sponges from Curacao and other Caribbean localities. Part II. Haplosclerida. Stud. Fauna Curacao Caribb. Isl. 62(191):1–173) encrusting on a Plakortis sp. (Class Demospongiae, Order Homosclerophorida, Family Plakinidae) (Diaz and Van Soest 1994), in an apparent symbiotic association. The sponges form an amorphous to hemispherical mass with oscules irregularly distributed over the surface. The color was dark brown both externally and internally. The consistency was firm. Spicules are strongyles and diods, distributed throughout the ectosome and choanosome. The choanosome is characteristic for the genus Strongylophora (Van Soest, 1980), however, the sample lacks strongylote microscleres. A taxonomic reference specimen is deposited at the Harbor Branch Oceanographic Museum (HBOM catalog number 003:00966, sample number 1-VI-93-4-002).

19

Compound 5

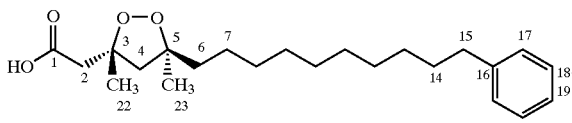

Purification of compound 5. The frozen sponge (75 g wet weight) was extracted by blending with EtOH (1.5 L). The combined EtOH extracts were concentrated to dryness (5.7 g) and partitioned between 1:1 n-BuOH/H$_2$O. The n-BuOH partition was concentrated to dryness (3.03 g) and a portion of this (337 mg) was further purified via vacuum flash column chromatography on a Si gel (Kieselgel 60H) stationary phase using a step gradient of heptane and heptane/EtOAc as eluent. The fraction which eluted with 75% EtOAc-heptane 3:1 (v/v), was further separated by HPLC (Whatman Partisil 10 ODS-3, 10×250 mm) using MeOH/H$_2$O (90:10 v/v, 5 mL/min.) to yield 5 (4.7 mg, retention time 5.2 minutes).

Structural Data for Compound 5:

$^1$H NMR (CDCl$_3$): δ 7.25 (2H, m, H-18), 7.15 (2H, d, J=7.2, H-17), 7.13 (1H, m, H-19), 2.74 (1H, d, J=15.3, H-2a), 2.69 (1H, d, J=15.3, H-2b), 2.58 (2H, t, J=8.1, H-15), 2.48 (1H, d, J=12.8, H-4a), 2.13 (1H, d, J=12.8, H-4b), 1.50–1.60 (m, H-6, 14), 1.46 (3H, s, H-20), 1.32 (3H, s, H-21), 1.20–1.30 (m, H-7 to 13).

$^{13}$C NMR (CDCl$_3$): δ 176.06 (s, C-1), 142.90 (s, C-16), 128.37 (d, C-17 or 18), 128.19 (d, C-18 or 17), 125.52 (d, C-19), 86.80 (s, C-5), 83.61 (s, C-3), 55.47 (t, C-4), 44.10 (t, C-2), 38.78 (t, C-6), 35.97 (t, C-15), 31.48 (t, C-14), 29.30–30.03 (t, C-8 to 13), 24.84 (t, C-7), 24.70 (q, C-20), 23.72 (q, C-21).

HRFABMS: m/z 377.2683 for C$_{23}$H$_{37}$O$_4$ [M+H]$^+$ (calculated 377.2693) m/z 399.2511 for C$_{23}$H$_{36}$NaO$_4$ [M+Na]$^+$ (calculated 399.2513)

EXAMPLE 5

Purification and Structural Data for Compound 6

Collection of Sponge Material. The sponge was collected at a depth of 75 feet in the off Long Bay, Negril, (latitude 18°17.25'N., longitude 78°22.10'W). It was frozen immediately after collection, and kept frozen until used.

Taxonomy of Source Organism. The sponge is identified as *Plakortis halichondrioides* (Phylum: Porifera, Class Demospongiae, Order Homosclerophorida, Family Plakinidae) (Diaz and Van Soest, 1994). The sponge was thickly encrusting. Color in life was black, both externally and internally. The surface of the sponge was smooth and the consistency was firm and dense. Spicules are diods. A taxonomic reference specimen is deposited at the Harbor Branch Oceanographic Museum (HBOM catalog number 003:00968), sample number 22-VIII-93-1-002).

Purification of Compounds. Purification: The frozen *Plakortis halichondrioides* (50 g wet wt) was diced and extracted with EtOH (5×200 mL). The crude extract was concentrated to dryness (2.57 g) and partitioned between 1:1 EtOAc/H$_2$O, the polar phase was further partitioned between n-BuOH and H$_2$O. The n-BuOH partition was concentrated to dryness (536 mg) and was further purified via vacuum flash column chromatography on a Si gel (Kieselgel 60H) stationary phase using a step gradient of heptane and heptane/EtOAc as eluent. The fractions 4 (40 mg) which eluted with 60% EtOAc was responsible for the antifungal activity of the sponge. Thirty-five (35) mg was taken for further purification by reversed-phase HPLC (Vydac Protein and Peptide C18 column, 10×250 mm, Solvent A: 10% acetonitrile in water v/v; Solvent B: 100% acetonitrile; t=0 minutes A:B 70:30; t=45 A:B 0:100; t=50 A:B 0:100; flow=3 ml/min; Detected by UV absorption observed at 210 nm] 9.4 mg of compound 6 (retention time=30.03 minutes) was obtained.

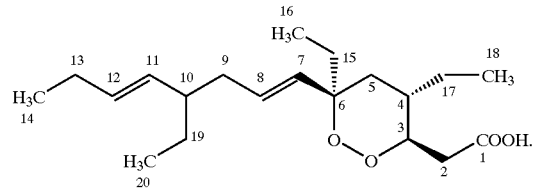

$^1$H NMR (CDCl$_3$): δ 5.44 (1H, dt, J=6.5, 15 Hz, H-8), 5.42 (1H, d, J=15 Hz, H-7), 5.38 (1H, dt, J=6.5, 15 Hz, H-12), 5.14 (1H, dd, J=8.5, 15 Hz, H-11), 4.16 (1H, ddd, J=3, 9, 9 Hz, H-3), 2.64 (1H, dd, J=3, 16 Hz, H-2a), 2.29 (1H, dd, J=9, 16 Hz, H-2b), 2.12 (m, H-9a), 2.05 (m, H-9b), 2.00 (m, H-5eq), 1.97 (2H, q, J=7 Hz, H-13), 1.90 (m, H-10), 1.58 (1H, m, H-4), 1.46 (m, H-17a, 19a), 1.38 (m, H-15a), 1.26 (m, H-5ax, H-19b), 1.18 (m, H-15b), 1.09 (m, H-17b), 0.95 (3H, t, J=7.5 Hz, H-14), 0.89 (3H, t, J=7.5 Hz, H-18), 0.83 (3H, t, J=7.5 Hz, H-16), 0.81 (3H, t, J=7.5 Hz, H-20).

$^{13}$C NMR (CDCl$_3$): δ 175.93 (s, C-1), 132.94 (d, C-11), 132.71 (d, C-8), 132.08 (d, C-12), 130.03 (d, C-7), 84.26 (s, C-6), 81.88 (d, C-3), 44.50 (d, C-10), 38.23 (t, C-9), 36.85 (d, C-4), 36.24 (t, C-5), 36.11 (t, C-2), 32.96 (t, C-19), 27.50 (t, C-15), 25.66 (t, C-13), 24.00 (t, C-17), 14.14 (q, C-14), 11.58 (q, C-20), 10.51 (q, C-18), 7.31 (t, C-16).

IR (CHCl$_3$): 2962, 2911, 2866, 1713, 1456, 968, 670 cm$^-$.

HRFABMS: m/z 361.22377 for C$_{20}$H$_{34}$O$_4$Na [M+Na]$^+$ (calculated 361.2355).

EXAMPLE 6

Antifungal Microtiter Broth Assay

Each well of a 96-well microtiter plate contained 200 μL of inoculum of *C. albicans* or *A. fumigatus* and 0.1 to 125 μg/mL of marine extract in DMSO. Controls for each assay were 0.025 to 16 μg/mL of amphotericin B, and 2 μL of DMSO. Culture plates were incubated for 24 or 48 hours (for *C. albicans* and *A. fumigatus* respectively) at 37° C., 120 rpm and scored visually using a light microscope. Growth in sample wells was compared to growth in control wells containing 2 μL DMSO and inoculum (2 μL of DMSO did not inhibit growth compared to controls grown in the absence of DMSO). Percent inhibition was estimated. The Minimum Inhibitory Concentration was determined. Samples were considered active if they inhibited 50% or more growth. The MIC of amphotericin B was 0.25–1.0 μg/mL, which agrees with published values (NCCLS. *Reference Method for Broth Dilution Antifungal Susceptibility Testing of Yeasts; Tenative Standard*. Protocol M27-T. Vol. 12(25), Wayne, P. A., 1995).

Antifungal activity for compounds 1–6.

TABLE 1

Data for Pure Compounds

| Compound | Candida albicans µg/ml | | Aspergillus fumigatus µg/ml | |
|---|---|---|---|---|
| | $IC_{50}$ | $IC_{90}$ | $IC_{50}$ | $IC_{90}$ |
| Peroxyacid 1 | 25 | 25 | 25 | 25 |
| Peroxyacid 2 | 25 | 25 | 25 | 25 |
| Peroxyacid 3 | 31.2 | 62.5 | 62.5 | 62.5 |
| Peroxyacid 4 | 31.2 | 31.2 | 31.2 | 31.2 |
| Peroxyacid 5 | 0.25 | 0.25 | 0.5 | 0.5 |
| Peroxyacid 6 | 2 | 3.9 | 5.6 | 5.6 |

EXAMPLE 7

Formulation and Administration

The compounds of the invention are useful for various non-therapeutic and therapeutic purposes. It is apparent from the testing that the compounds of the invention are effective as fungicidal and/or fungistatic agents. The compounds can be used to inhibit unwanted fungal growth in the work areas of labs in humans or on plants. Also, the compounds can be used as ultraviolet screeners in the plastics industry since they effectively absorb UV rays. As disclosed herein, they can be used therapeutically for treating fungal infections in animals and humans.

Therapeutic application of the new compounds and compositions containing them can be contemplated to be accomplished by any suitable therapeutic method and technique presently or prospectively known to those skilled in the art. Further, the compounds of the invention have use as starting materials or intermediates for the preparation of other useful compounds and compositions.

The dosage administration to a host in the above indications will be dependent upon the identity of the infection, the type of host involved, its age, weight, health, kind of concurrent treatment, if any, frequency of treatment, and therapeutic ratio.

The compounds of the subject invention can be formulated according to known methods for preparing antifungal compositions. Formulations are described in detail in a number of sources which are well known and readily available to those skilled in the art. For example, Remington's Pharmaceutical Science by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as active ingredient, an effective amount of one or more of the subject compounds and one or more non-toxic, pharmaceutically acceptable carriers or diluents can be used by persons of ordinary skill in the art. In addition, the pharmaceutical composition can comprise one or more of the compounds as a first active ingredient plus a second active ingredient comprising a compound known in the art.

In accordance with this invention, pharmaceutically effective amounts of the compounds are administered sequentially or concurrently to the patient. The most effective mode of administration and dosage regimen of the compounds will depend upon the type of disease to be treated, the severity and course of that disease, previous therapy, the patient's health status, and the judgment of the treating physician. The compositions may be administered to the patient at one time or over a series of treatments.

Conventional modes of administration and standard dosage regimens may be used (see Gilman, A. G. et al. [eds.] The Pharmacological Basis of Therapeutics, pp. 697–713, 1482, 1489–91 [1980]; Physicians Desk Reference, 1986 Edition).

The compositions used in these therapies can also be in a variety of forms. These include, for example, solid, semi-solid, and liquid dosage forms, such as tablets, pills, powders, liquid solutions or suspension, suppositories, injectable and infusible solutions. The preferred form depends on the intended mode of administration and therapeutic application. The compositions also preferably include conventional pharmaceutically acceptable carriers and adjuvants which are known to those of skill in the art. Preferably, the compositions of the invention are in the form of a unit dose and will usually be administered to the patient one or more times a day.

The compounds of the subject invention may also be administered utilizing liposome technology, slow release capsules, implantable pumps, and biodegradable containers. These delivery methods can, advantageously, provide a uniform dosage over an extended period of time.

Examples of such carriers or diluents include ethanol, dimethyl sulfoxide, glycerol, silica, alumina, starch, and equivalent carriers and diluents. While effective amounts may vary, as conditions in which compositions are used vary, a minimal dosage required for activity is generally between 0.01 and 100 µg of the compound. To provide for the administration of such dosages for the desired therapeutic treatment, new pharmaceutical compositions of the invention will advantageously comprise between about 0.1% and 45%, and especially, 1 and 15% by weight of the total of one or more of the new compounds based on the weight of the total composition including carrier or diluent.

Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Once improvement of the patient's condition has occurred, a maintenance dose is administered if necessary. Subsequently, the dosage or the frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence of disease symptoms.

The compounds of the invention are useful for various non-therapeutic and therapeutic purposes. It is apparent from the testing that the compounds of the invention are effective for inhibiting cell growth. Because of the antiproliferative properties of the compounds, they are useful to prevent unwanted cell growth in a wide variety of settings including in vitro uses. They are also useful as standards and for teaching demonstrations. They can also be used as ultraviolet screeners in the plastics industry since they effectively absorb UV rays. As disclosed herein, they are also useful prophylactically and therapeutically for treating cancer cells in animals and humans.

Therapeutic application of the new compounds and compositions containing them can be accomplished by any suitable therapeutic method and technique presently or prospectively known to those skilled in the art. Further, the compounds of the invention have use as starting materials or intermediates for the preparation of other useful compounds and compositions.

The dosage administration to a host in the above indications will be dependent upon the identity of the cancer cells, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as an active ingredient, an effective amount of one or more of the new compounds and one or more non-toxic, pharmaceutically acceptable carrier or diluent. Examples of such carriers for use in the invention include ethanol, dimethyl sulfoxide, glycerol, silica, alumina, starch, and equivalent carriers and diluents.

To provide for the administration of such dosages for the desired therapeutic treatment, new pharmaceutical compositions of the invention will advantageously comprise between about 0.1% and 45%, and especially, 1 and 15%, by weight of the total of one or more of the new compounds based on the weight of the total composition including carrier or diluent. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for inhibiting a fungal infection wherein said method comprises administering to said fungus an antifungal amount of a compound, or a salt thereof, wherein said compound is selected from the group consisting of:

Compound 1

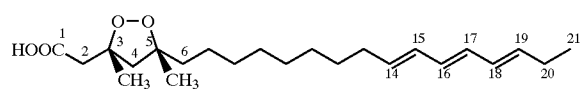

Compound 2

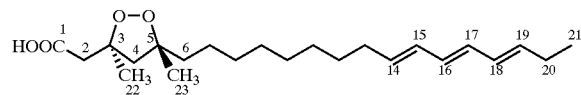

Compound 3

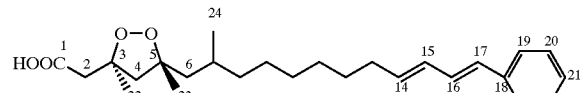

Compound 4

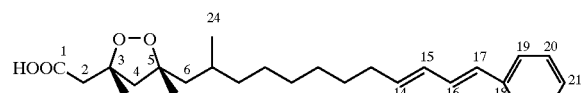

Compound 5

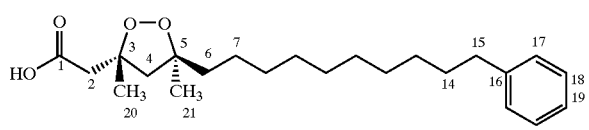

and

Compound 6

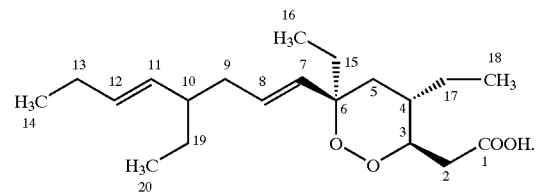

2. The method, according to claim 1, wherein said compound is

Compound 1

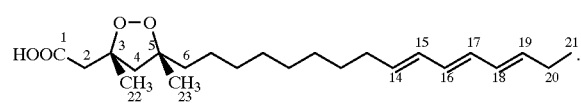

3. The method, according to claim 1, wherein said compound is

Compound 2

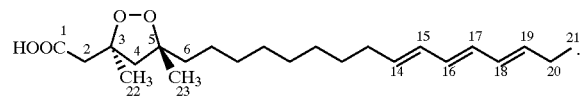

4. The method, according to claim 1, wherein said compound is

Compound 3

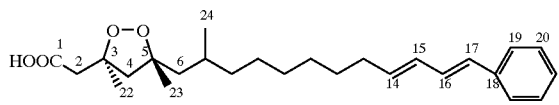

5. The method, according to claim 1, wherein said compound is

Compound 4

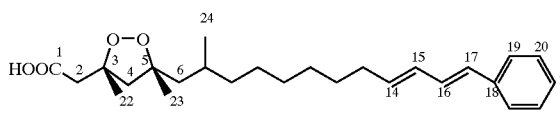

6. The method, according to claim 1, wherein said compound is

Compound 5

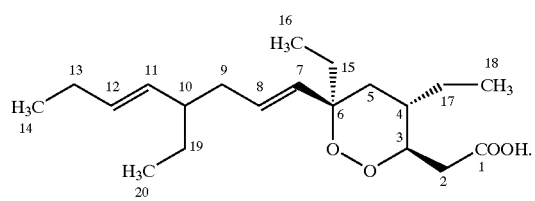

7. The method, according to claim 1, wherein said compound is

Compound 6

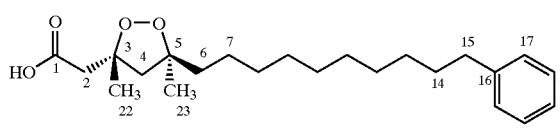

8. The method, according to claim 1, wherein said fungal infection is in or on an animal.

9. The method, according to claim 1, wherein said fungal infection is in or on a plant.

10. The method, according to claim 1, wherein said fungal infection is of food or cosmetics.

11. An antifungal compound, or a salt thereof, wherein said compound is selected from the group consisting of Compound 1

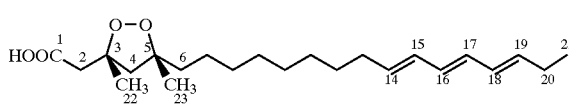

Compound 2

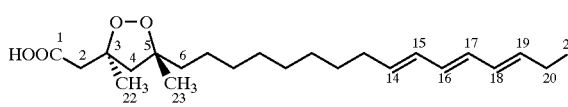

Compound 3

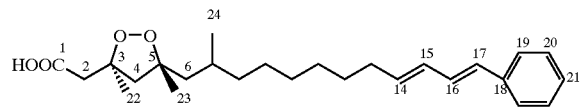

Compound 4

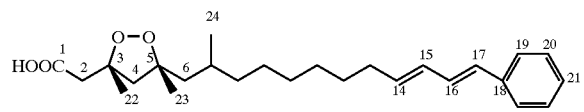

and

Compound 6

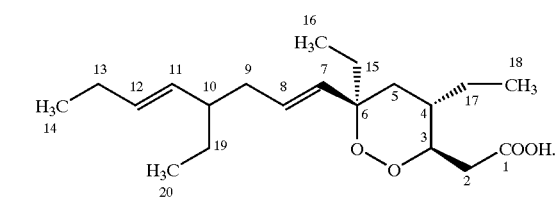

12. The compound, according to claim 11, wherein said compound is

Compound 1

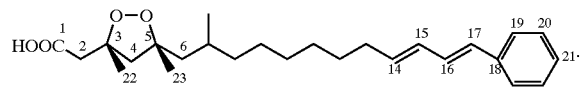

13. The compound, according to claim 11, wherein said compound is

Compound 2

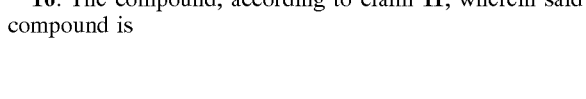

14. The compound, according to claim 11, wherein said compound is

Compound 3

15. The compound, according to claim 11, wherein said compound is

Compound 4

16. The compound, according to claim 11, wherein said compound is

Compound 6

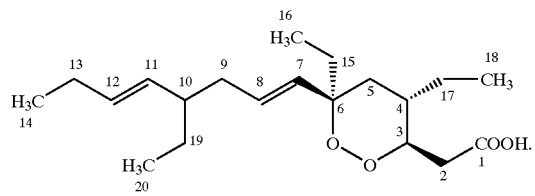

17. A pharmaceutical composition comprising a pharmaceutically-acceptable carrier and an antifungal compound, or a salt thereof, wherein said compound is selected from the group consisting of Compound 1

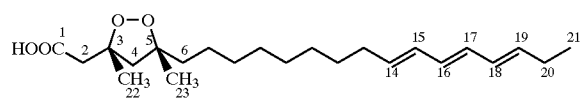

Compound 2

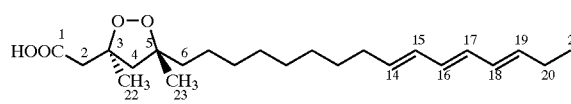

Compound 3

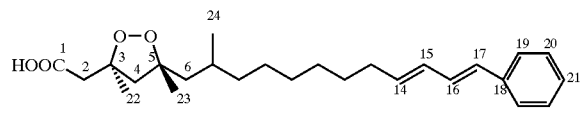

Compound 4

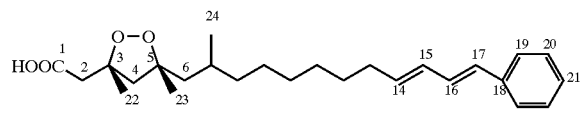

Compound 5

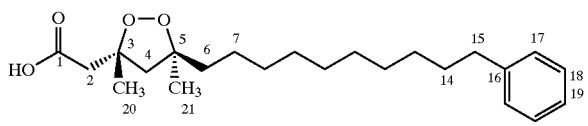

and
Compound 6

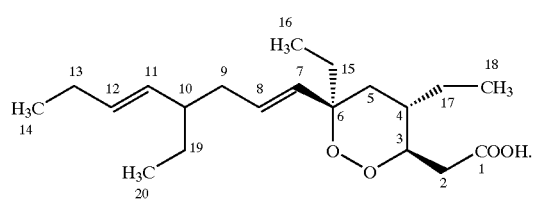

18. The pharmaceutical composition, according to claim 17, wherein said compound is Compound 1

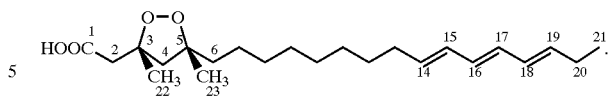

19. The pharmaceutical composition, according to claim 17, wherein said compound is Compound 2

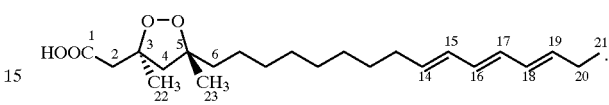

20. The pharmaceutical composition, according to claim 17, wherein said compound is Compound 3

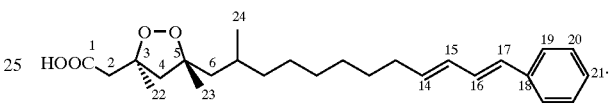

21. The pharmaceutical composition, according to claim 17, wherein said compound is Compound 4

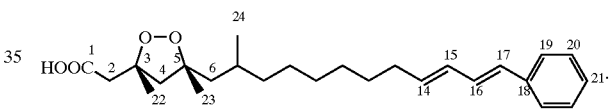

22. The pharmaceutical composition, according to claim 17, wherein said compound is Compound 5

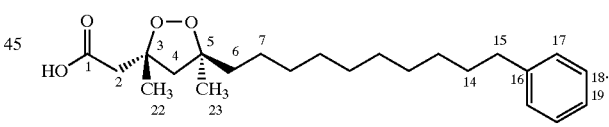

23. The pharmaceutical composition, according to claim 17, wherein said compound is Compound 6

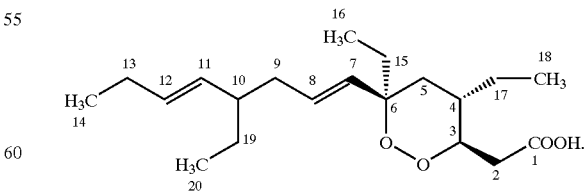

24. An agricultural composition comprising an antifungal compound, or a salt thereof, and an appropriate agricultural carrier; wherein said compound is selected from the group consisting of:

Compound 1

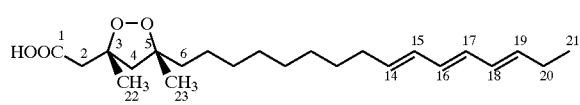

Compound 2

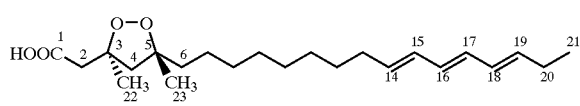

Compound 3

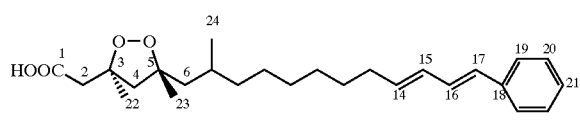

Compound 4

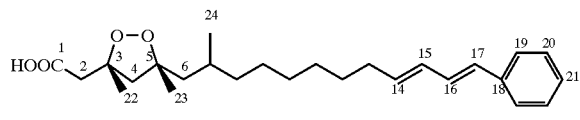

Compound 5

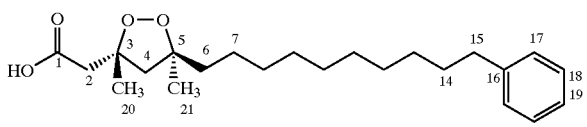

and

Compound 6

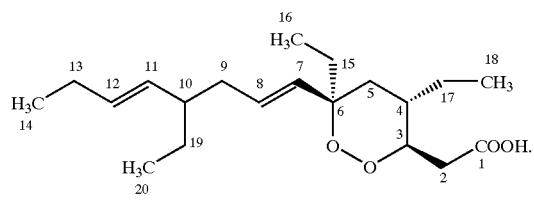

25. The agricultural composition, according to claim 24, wherein said compound is Compound 1

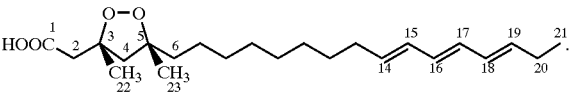

26. The agricultural composition, according to claim 24, wherein said compound is
Compound 2

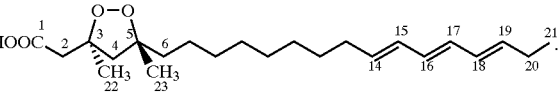

27. The agricultural composition, according to claim 24, wherein said compound is
Compound 3

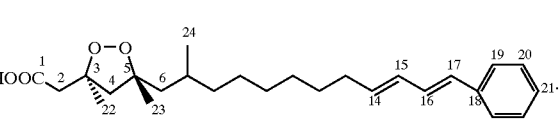

28. The agricultural composition, according to claim 24, wherein said compound is
Compound 4

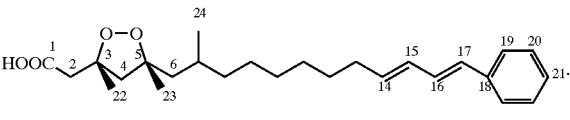

29. The agricultural composition, according to claim 24, wherein said compound is
Compound 5

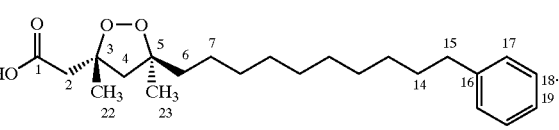

30. The agricultural composition, according to claim 24, wherein said compound is
Compound 6

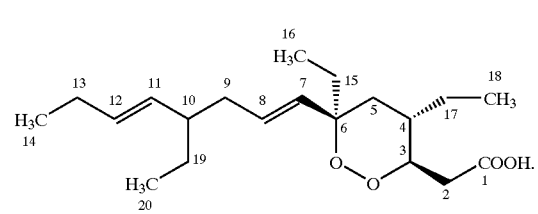

* * * * *

UNITED STATES PATENT AND TRADEMARK OFFICE
CERTIFICATE OF CORRECTION

PATENT NO. : 6,521,661 B1  
DATED : July 20, 2001  
INVENTOR(S) : Ying Chen et al.

Page 1 of 1

It is certified that error appears in the above-identified patent and that said Letters Patent is hereby corrected as shown below:

<u>Column 7,</u>  
Line 45, " " should read --  --

Line 50, " " should read --  --

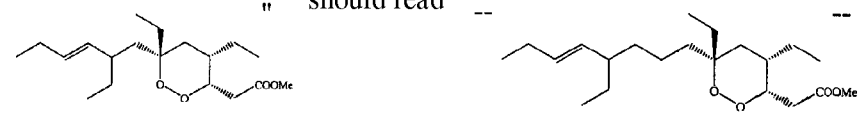

<u>Column 8,</u>  
Line 50, " " should read --  --

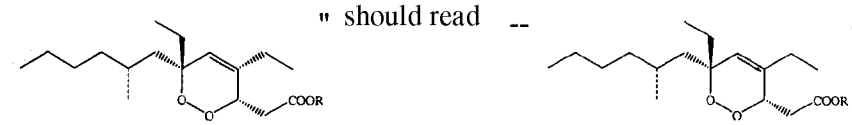

Signed and Sealed this

Thirtieth Day of September, 2003

JAMES E. ROGAN  
*Director of the United States Patent and Trademark Office*